United States Patent
Nakamura et al.

(10) Patent No.: US 10,597,343 B2
(45) Date of Patent: Mar. 24, 2020

(54) COMPOSITION INCLUDING FLUOROMETHANE AND METHOD FOR PRODUCING SAME

(71) Applicant: DAIKIN INDUSTRIES, LTD., Osaka (JP)

(72) Inventors: Shingo Nakamura, Osaka (JP); Yuusuke Etou, Osaka (JP); Seiji Takubo, Osaka (JP); Katsuya Nakai, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/577,963

(22) PCT Filed: Jun. 3, 2016

(86) PCT No.: PCT/JP2016/066535
§ 371 (c)(1),
(2) Date: Nov. 29, 2017

(87) PCT Pub. No.: WO2016/195055
PCT Pub. Date: Dec. 8, 2016

(65) Prior Publication Data
US 2018/0141886 A1  May 24, 2018

(30) Foreign Application Priority Data
Jun. 3, 2015 (JP) ................. 2015-113388

(51) Int. Cl.
C07C 17/361 (2006.01)
B01J 21/04 (2006.01)
C07C 19/08 (2006.01)
B01J 6/00 (2006.01)

(52) U.S. Cl.
CPC ............ C07C 17/361 (2013.01); B01J 6/008 (2013.01); B01J 21/04 (2013.01); C07C 19/08 (2013.01); C07C 2521/04 (2013.01)

(58) Field of Classification Search
CPC .................................. C07C 17/361
See application file for complete search history.

(56) References Cited

U.S. PATENT DOCUMENTS 3,445,541 A * 5/1969 Heckelsberg ........... C07C 5/333
585/630
2015/0299088 A1  10/2015 Nakamura et al.
2017/0334814 A1  11/2017 Etou et al.

FOREIGN PATENT DOCUMENTS

| | | | | |
|---|---|---|---|---|
| CN | 102762525 A | * | 10/2012 | ........... C07C 17/361 |
| JP | 10-57765 | | 3/1998 | |
| JP | 2012-180285 | | 9/2012 | |
| JP | 2014-114277 | | 6/2014 | |
| JP | 2016-84293 | | 5/2016 | |
| WO | WO-2014077246 A1 | * | 5/2014 | ........... C07C 17/361 |
| WO | 2016/063939 | | 4/2016 | |

OTHER PUBLICATIONS

CN102762525A, Oct. 31, 2012, pp. 1-19; English translation (Year: 2012).*
WO2014077246A1, May 22, 2014, pp. 1-15 (Year: 2014).*
International Search Report dated Sep. 6, 2016 in International (PCT) Application No. PCT/JP2016/066535.
England, "Catalytic conversion of Fluoroalkyl Alkyl Ethers to Carbonyl Compounds", Journal of Organic Chemistry, vol. 49, No. 21, 1984, pp. 4007-4008.
"Product Databook", Sumitomo Chemical Alumina Products Dept., 2014, vol. 3, Ed. 1, pp. 1-14.

* cited by examiner

*Primary Examiner* — Medhanit W Bahta
(74) *Attorney, Agent, or Firm* — Wenderoth, Lind & Ponack, L.L.P.

(57) ABSTRACT

An object of the present invention is to provide a composition containing fluoromethane having high purity. A method for producing fluoromethane, comprising: pyrolyzing in a gas phase a fluorine-containing methyl ether represented by Formula (1):

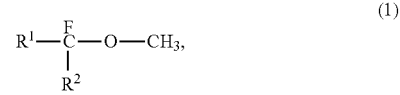

(1)

wherein $R^1$ and $R^2$ are the same or different, and each represents an optionally substituted linear or branched monovalent aliphatic hydrocarbon group, an optionally substituted monovalent aromatic hydrocarbon group, an optionally substituted monovalent cyclic aliphatic hydrocarbon group, hydrogen, or halogen, in the presence of an alumina catalyst to thereby obtain a mixed gas containing fluoromethane and acid fluoride, wherein: the alumina catalyst contains chlorine in an amount of 1.0 wt % or less.

2 Claims, No Drawings

COMPOSITION INCLUDING FLUOROMETHANE AND METHOD FOR PRODUCING SAME

TECHNICAL FIELD

The present invention relates to a composition comprising fluoromethane useful as a dry etching gas, and a method for producing the composition.

BACKGROUND ART

Hydrofluorocarbons are useful as etching gases for the microfabrication of semiconductors, liquid crystals, and the like. In particular, fluoromethane ($CH_3F$) is drawing attention as an etching gas for forming state-of-the-art microstructures.

A known method for producing fluoromethane is, for example, a method in which a mixed gas containing fluoromethane and acid fluoride is obtained by pyrolyzing a starting compound in a gas phase in the presence of an alumina catalyst (Patent Document 1).

CITATION LIST

Patent Documents

Patent Document 1: JP2014-114277A

SUMMARY OF INVENTION

Technical Problem

An object of the present invention is to provide a composition containing fluoromethane having high purity.

Solution to Problem

The inventors of the present invention conducted extensive research to attain the above object. It is known that an alumina catalyst is treated with hydrochloric acid in some cases to increase the reaction activity. As a result of the research, the present inventors found contamination of a small amount of methane, ethane, propane, methyl chloride, and the like in the reaction product due to the hydrochloric acid treatment. Of these contaminants, it is difficult to remove methyl chloride, even if the amount thereof is only several ppm. Regarding this problem, the present inventors discovered that the contamination of impurities in the final product may be prevented by using an alumina catalyst untreated with hydrochloric acid. The present invention has been completed upon further trial and error based on these findings, and encompasses the following items.

Item 1.

A method for producing fluoromethane, comprising:
pyrolyzing in a gas phase a fluorine-containing methyl ether represented by Formula (1):

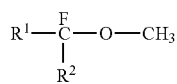
(1)

wherein $R^1$ and $R^2$ are the same or different, and each represents an optionally substituted linear or branched monovalent aliphatic hydrocarbon group, an optionally substituted monovalent aromatic hydrocarbon group, an optionally substituted monovalent cyclic aliphatic hydrocarbon group, hydrogen, or halogen,
in the presence of an alumina catalyst to thereby obtain a mixed gas containing fluoromethane and acid fluoride,
wherein:
the alumina catalyst contains chlorine in an amount of 1.0 wt % or less.

Item 2.

The method according to Item 1, wherein the catalyst is a γ-alumina catalyst.

Item 3.

A composition comprising fluoromethane obtainable by the method of Item 1 or 2.

Item 4.

A composition comprising fluoromethane in an amount of 99.999 mol % or more based on the total weight of the composition.

Item 5.

The composition according to Item 3 or 4, wherein the composition is used as a dry etching gas.

Item 6.

An alumina catalyst containing chlorine in an amount of 1.0 wt % or less, for use in a method for producing fluoromethane,
the method comprising pyrolyzing a starting compound in a gas phase in the presence of a catalyst to thereby obtain a mixed gas containing fluoromethane and acid fluoride.

Item 7.

The alumina catalyst according to Item 6, wherein the alumina catalyst is a γ-alumina catalyst.

Advantageous Effects of Invention

The present invention is capable of providing a composition containing fluoromethane having high purity.

DESCRIPTION OF EMBODIMENTS

1. Method for Producing Fluoromethane

The method for producing fluoromethane according to the present invention comprises the step of pyrolyzing a starting compound in a gas phase in the presence of an alumina catalyst to thereby obtain a mixed gas containing fluoromethane and acid fluoride, wherein the alumina catalyst contains chlorine in an amount of 1.0 wt % or less.

(1) Pyrolysis Reaction

The reaction of performing pyrolysis in a gas phase to thereby obtain a mixed gas containing fluoromethane and acid fluoride has already been known, as disclosed, for example, in JP2014-114277A and the like.

(i) Starting Compound

The present invention uses a fluorine-containing methyl ether represented by Formula (1) as a starting compound.

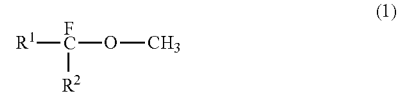
(1)

(wherein $R^1$ and $R^2$ are the same or different, and each represents an optionally substituted linear or branched monovalent aliphatic hydrocarbon group, an optionally substituted monovalent aromatic hydrocarbon group, an optionally substituted monovalent cyclic aliphatic hydrocarbon group, hydrogen, or halogen).

The method for producing fluorine-containing methyl ether to be used as a starting compound is not particularly limited, and compounds obtained by any methods may be used.

In Formula (1) above, preferably, $R^1$ and $R^2$ are the same or different, and each represents an optionally substituted $C_{1-30}$ linear or branched monovalent aliphatic hydrocarbon group, an optionally substituted $C_{6-12}$ monovalent aromatic hydrocarbon group, or an optionally substituted $C_{6-12}$ monovalent cyclic aliphatic hydrocarbon group. More preferably, $R^1$ and $R^2$ are the same or different, and each represents an optionally substituted $C_{1-10}$ linear or branched monovalent aliphatic hydrocarbon group, an optionally substituted $C_{6-10}$ monovalent aromatic hydrocarbon group, or an optionally substituted $C_{6-10}$ monovalent cyclic aliphatic hydrocarbon group.

Examples of the above $C_{1-10}$ linear or branched monovalent aliphatic hydrocarbon group include, but are not particularly limited to, $C_{1-10}$ alkyl group and the like.

More specifically, examples of $C_{1-10}$ alkyl include methyl, ethyl, trimethyl, propyl, 2-methylethyl, hexyl, octyl, and the like.

The $C_{1-10}$ alkyl is preferably $C_{1-6}$ alkyl, more preferably $C_{1-4}$ alkyl, further preferably $C_{1-3}$ alkyl.

Examples of $C_{6-10}$ monovalent aromatic hydrocarbon group include, but are not particularly limited to, phenyl, methyl phenyl, ethyl phenyl, and the like.

Examples of $C_{6-10}$ monovalent cyclic aliphatic hydrocarbon group include, but are not particularly limited to, cyclohexyl, methyl cyclohexyl, ethyl cyclohexyl, and the like.

In the above formula, at least one hydrogen atom of the monovalent aliphatic hydrocarbon group, monovalent aromatic hydrocarbon group, or monovalent cyclic aliphatic hydrocarbon group may be replaced by at least one heteroatom selected from the group consisting of fluorine, chlorine, and bromine; or all hydrogen atoms may be replaced.

In the above formula, the halogen is preferably fluorine, chlorine, or bromine; and more preferably fluorine.

Examples of specific compounds that can be used as starting compounds include, but are not limited to, 1,1,3,3,3-pentafluoro-2-trifluoromethylpropyl methyl ether and the like.

In particular, perfluoroisobutylene (($CF_3)_2C=CF_2$), which is obtained as a by-product when hexafluoropropene used as a starting compound of fluororesin is produced, has hitherto been discarded as waste; however, 1,1,3,3,3-pentafluoro-2-trifluoromethylpropyl methyl ether can be obtained by reacting perfluoroisobutylene with methanol. Use of the thus-obtained 1,1,3,3,3-pentafluoro-2-trifluoromethylpropyl methyl ether as a starting compound in the present invention allows for effective utilization of waste, and enables the desired product to be produced inexpensively using the low-cost starting compound. In the present invention, the phrase stating that 1,1,3,3,3-pentafluoro-2-trifluoromethylpropyl methyl ether used as a starting compound is "obtained by reacting perfluoroisobutylene and methanol" is limited to the meaning that the 1,1,3,3,3-pentafluoro-2-trifluoromethylpropyl methyl ether is obtained by said reaction, and is not obtained by other methods. The method for obtaining 1,1,3,3,3-pentafluoro-2-trifluoromethylpropyl methyl ether by reacting perfluoroisobutylene and methanol is a known method, and may be conducted in accordance with known reaction conditions. For example, the reaction may be performed in accordance with the method disclosed in JP2001-506261A.

Although the method is not particularly limited, fluoromethane and 3,3,3-trifluoro-2-(trifluoromethyl)propanoyl fluoride may be obtained by, for example, pyrolyzing 1,1,3,3,3-pentafluoro-2-trifluoromethylpropyl methyl ether, which is a starting compound. By rectifying this mixed gas, a composition containing fluoromethane at high purity may be obtained. The present inventors clarified that this composition contains a small amount of HFC-1225zc as a contaminant.

(ii) Catalyst

An alumina catalyst containing a small amount of chlorine is used as a catalyst. Alumina catalysts include those containing chlorine as an impurity, or those treated with hydrochloric acid to improve the reaction activity. Therefore, these alumina catalysts contain chlorine as a contaminant. If the pyrolysis reaction of the present invention is performed using an alumina catalyst thus containing chlorine, the reaction product contains a small amount of methane, ethane, propane, methyl chloride, and the like as contaminants. In particular, the present inventors confirmed difficulties in removing even several ppm of methyl chloride. Therefore, the present invention is characterized by using an alumina catalyst containing a small amount of chlorine. Using such an alumina catalyst prevents the contamination of impurities in the reaction product.

In other words, the present invention uses an alumina catalyst containing chlorine in an amount of 1.0 wt % or less, preferably 0.5 wt % or less, more preferably 0.1 wt % or less; further preferably, the present invention uses an alumina catalyst with a chlorine content of no more than the detection limit.

In the present invention, the content of contaminants in the alumina catalyst is measured as follows using glow-discharge mass spectrometry. The surface of an alumina catalyst sample is sputtered by glow discharge under an Ar atmosphere, and the emitted neutral particles are ionized by the collision with Ar and electrons in the plasma; and the ions are measured by a high-resolution mass spectrometer.

In the present invention, the pore volume may be measured by a commonly used gas adsorption method using a device from Nippon-bel.co.jp, or a similar device.

α-alumina and activated alumina and the like may be used as an alumina catalyst. Examples of activated alumina include ρ-alumina, χ-alumina, κ-alumina, η-alumina, pseudo-γ-alumina, γ-alumina, δ-alumina and θ-alumina. Of these, γ-alumina and η-alumina are preferable, and γ-alumina is particularly preferable. Further, silica alumina ($SiO_2/Al_2O_3$), a composite oxide, may also be used as a catalyst. The proportion of silica $SiO_2$ in silica alumina is preferably 20 to 90 wt %, and more preferably 50 to 80 wt %.

The larger the pore volume of the catalyst, the higher the activity. The pore volume of the catalyst is preferably 0.4 ml/g or more, and particularly preferably 0.6 ml/g or more.

Further, the catalyst may have deposited thereon fluorides of alkali metals and alkaline earth metals, such as KF, NaF, and $MgF_2$.

In the present invention, fluorinated alumina catalysts may also be used. There is no particular limitation on the method for obtaining the above-mentioned fluorinated alumina catalysts. For example, the fluorinated alumina catalysts can be obtained by bringing the above-described alumina catalysts into contact with anhydrous hydrogen fluoride or fluorocarbon while heating to allow a fluorination reaction to proceed. The method for bringing the alumina catalysts into contact with hydrogen fluoride is not particularly limited, and may be a continuous flow method in which hydrogen fluoride is allowed to flow through a reaction tube containing the catalyst, or a batch method in which hydrogen fluoride or fluorocarbon is enclosed in a container containing the catalyst. In particular, the flow method is preferable in terms of a short treatment time.

The fluorocarbon is preferably one with a large number of fluorine atoms and a small number of carbon atoms. Examples of fluorocarbon include trifluoromethane, difluorochloromethane, octafluoroethane, and the like.

The degree of fluorination of such an alumina catalyst is not particularly limited; those having a fluorine content of about 5 to 50 wt % based on the total weight of fluorinated alumina catalyst are preferably used.

The temperature of the fluorination treatment for such an alumina catalyst is preferably higher than that of the below-described pyrolysis reaction; and is, for example, preferably about 150 to 500° C., more preferably about 200° C. to 400° C., further preferably about 250° C. to 350° C. An excessively low temperature in the fluorination treatment decreases the effect of the catalyst because of insufficient fluorination, whereas an excessively high temperature in the fluorination treatment additionally requires a heat-resistant material; thus, it is not practical.

(iii) Pyrolysis Reaction Conditions

The pyrolysis reaction of fluorine-containing methyl ether may be advanced by bringing the fluorine-containing methyl ether into contact with the above-described catalyst in a gas phase in the presence of the catalyst. There is no particular limitation on the specific method: an example is a method in which the catalyst is placed in a tubular flow reactor, and fluorine-containing methyl ether used as a starting material is introduced to the reactor and brought into contact with the catalyst in a gas phase.

If the temperature of the pyrolysis reaction is excessively low, the conversion of the starting material tends to decrease. If the temperature of the pyrolysis reaction is excessively high, impurities tend to increase. Thus, the temperature of the pyrolysis reaction is preferably about 100° C. to 400° C., further preferably about 100° C. to 300° C., particularly preferably about 100° C. to 250° C.

An excessively low pressure in the reactor tube during the pyrolysis reaction complicates the operation because of the possible contamination of air etc., whereas an excessively high pressure in the reactor tube during the pyrolysis reaction requires that the pressure resistance of the equipment be considered, and increases the possibility of leakage. Considering these points, the pressure in the reactor tube during the pyrolysis reaction is preferably about 0.05 to 1 MPa, more preferably about 0.1 to 0.5 MPa, and particularly preferably, in terms of reaction operation, about atmospheric pressure (about 0.1 MPa).

There is no particular limitation on the contact time for causing the reaction. The contact time represented by W/F (g·sec/cc), i.e., the ratio of the amount of the catalyst W (g) relative to the flow rate F (the flow rate at 0° C. and 1 atm (about 0.1 MPa): cc/sec) of the starting material gas, i.e., fluorine-containing methyl ether that is supplied to the reactor, is preferably about 1 to 100 g·sec/cc, more preferably about 1 to 50 g·sec/cc, and even more preferably about 5 to 30 g·sec/cc. If the contact time is excessively long, it takes a long time to obtain the product. Thus, to increase the amount of production, it is preferred that the contact time be shortened. However, if the contact time is excessively short, the conversion tends to decrease. Thus, the contact time may be selected so that the highest productivity is obtained in terms of the conversion of the starting material and the selectivity of the desired product, according to the type of catalyst to be used, the amount of the catalyst, the reaction conditions, and the like.

In general, it is desirable to conduct the reaction by selecting the contact time so that the conversion becomes 100%, according to the type of catalyst to be used, the amount of the catalyst, the reaction conditions, and the like.

(iv) Mixed Gas

As a result of a pyrolysis reaction, a mixed gas containing fluoromethane and acid fluoride is obtained. The mixed gas contains, in addition the desired product, i.e., fluoromethane (boiling point: −79° C.), acid fluoride that is simultaneously produced by the pyrolysis. The mixed gas may further contain at least one member of starting compound, by-products, and impurities. Although it varies depending on the starting compound, examples of by-products include propene (boiling point: −47.7° C.), propene pentafluoride (boiling point: −21.1° C.), propane (boiling point: −1.4° C.), and the like.

2. Purification

By rectifying the mixed gas containing fluoromethane and acid fluoride obtained by the above pyrolysis reaction, it is possible to obtain a composition containing fluoromethane at high purity.

The method for separating the fluoromethane and the acid fluoride contained in the resulting product is not particularly limited; for example, by cooling the gas produced by the pyrolysis reaction, it is possible to separate it into a gas component and a liquid component, the gas component containing a low-boiling-point component that contains fluoromethane (boiling point: −79° C.) as a main component, and the liquid component containing a high-boiling-point component that contains acid fluoride as a main component and may further contain unreacted starting materials. In this case, although the cooling temperature is not particularly limited, for example, the temperature is preferably as low as possible so that the fluoromethane will not be condensed. For example, the gas may be cooled to a temperature at which a pressure less than the saturated vapor pressure of fluoromethane may be maintained in an enclosed space.

With this method, it is possible to separate a component containing fluoromethane as a gas component. The gas component may contain propene (boiling point of −47.7° C.), pentafluoropropene (boiling point of −21.1° C.), propane (boiling point of −1.4° C.), and the like, as impurities. However, these impurities can be easily separated by distillation since fluoromethane and these impurities have very different boiling points.

In addition, when the high-boiling-point component, which is obtained as a liquid component and contains acid fluoride as a main component, contains unreacted starting materials and the like, the unreacted starting materials and the like can be easily separated by distillation.

Further, to selectively obtain fluoromethane, the product obtained after the pyrolysis reaction may be brought into contact with water, an aqueous alkaline solution, or the like to dissolve acid fluoride in an aqueous phase, thereby removing the acid fluoride. This enables selective collection of fluoromethane.

In the above process, an alcohol may be used instead of water or an aqueous alkaline solution. Inexpensive alcohols are preferable in terms of cost. Examples of usable alcohols include methanol, ethanol, propanol, and the like. Of these, methanol is particularly preferable. Bringing the product into contact with an alcohol to produce an ester makes combustion treatment easier.

Further, by subjecting the mixed gas directly to the rectification, it is possible to obtain a composition containing fluoromethane at high purity. It is therefore not necessary to remove the acid fluoride before the purification by fractionation operations or washing with water or alcohol, and the fluoromethane can be easily separated from the acid fluoride.

The boiling point of acid fluoride is generally equal to or higher than room temperature; for example, the boiling point of 3,3,3-trifluoro-2-(trifluoromethyl)propanoyl fluoride is 32° C. Thus, the boiling point of acid fluoride is significantly higher than that of fluoromethane (boiling point: −79° C.). In the mixed gas, fluoromethane and acid fluoride are present at a molar ratio of 1:1. When the mixed gas is directly placed in an environment at around room temperature, acid fluoride is expected to be condensed. However, the present inventors unexpectedly found a phenomenon in which an interaction occurred between these two components, and the mixed gas as a whole acted as a gas that was not condensed, even at around room temperature (under predetermined pressure conditions). By taking advantage of these findings in the present invention, the mixed gas can be directly subjected to a rectification operation to efficiently separate fluoromethane.

Preferably, the mixed gas obtained in the pyrolysis reaction is supplied to a rectification column. The supply of the mixed gas is preferably conducted at a pressure exceeding atmospheric pressure. This facilitates the transfer of the mixed gas to the rectification column. The pressure during transfer is more preferably 0.2 MPa to 0.15 MPa. At a pressure within this range, the mixed gas can be effectively supplied to the rectification column, while avoiding the condensation of the mixed gas.

There is no particular limitation on the rectification. In general, two rectification columns are provided, and low-boiling-point components, such as methane or ethylene, are extracted from the top of a first rectification column. The remaining components containing fluoromethane and acid fluoride are obtained from the bottom of the column, and further supplied to a second rectification column. Then, fluoromethane can be extracted from the top of the column. In this method, the purity of the fluoromethane finally obtained from the top of the second rectification column is 99.999 mol % or more.

2. Composition

The composition of the present invention is a composition that can be produced by the production method of the present invention, and is a composition containing 99.999 mol % or more of fluoromethane based on the total weight of the composition.

In the above method, the weight-based proportions of the respective components based on the total weight of the composition are determined by gas chromatographic analysis (GC). Specifically, the proportions are determined as follows.

A quantitative analysis is performed using a general internal standard method to determine the concentrations. Difluoro methane (HFC-32) and benzotrifluoride are used as internal standard substances respectively for a low-boiling-point compound and a high-boiling-point compound. Several kinds of standard samples containing known contents (molar ratios) of the internal standard substance and the test sample are analyzed, and a calibration curve of molar ratio versus peak area ratio is plotted. An internal standard substance of a known amount is added to a sample whose fluoromethane content is unknown, and the peak area ratio on the gas chromatogram is measured, thereby calculating the fluoromethane content from the relative mol sensitivity.

EXAMPLES

The present invention is described in more detail below with reference to Examples.

Example 1

1,1,3,3,3-pentafluoro-2-trifluoromethylpropyl methyl ether (OIME) in a gas state was flowed into a reactor filled with a γ-alumina catalyst A free of chlorine heated to 150° C., and pyrolyzed. The conversion of OIME was 84%.

The composition of the collected reaction product was as follows: 41.6 mol % of $CH_3F$, 0.015% of HFO-1225zc (1,1,3,3,3-pentafluoro propene), 0.022 mol % of HFC-236fa (1,1,1,3,3,3-hexafluoro propane), 16.4 mol % of OIME, 41.7 mol % of acid fluoride, 0.21 mol % of HIME (1,1,1,3,3,3-hexafluoro-2-methoxy propane). The rest was other components. Methyl chloride was not detected.

Example 2

1,1,3,3,3-pentafluoro-2-trifluoromethylpropyl methyl ether (OIME) in a gas state was flowed into a reactor filled with a γ-alumina catalyst B free of chlorine heated to 150° C., and pyrolyzed. The conversion of OIME was 92%.

The composition of the collected reaction product was as follows: 0.002 mol % of methane, 0.0036 mol % of ethylene, 46.17 mol % of $CH_3F$, 0.0092 mol % of propylene, 7.58 mol % of OIME, 46.17 mol % of acid fluoride, and 0.0615 mol % of other components. Methyl chloride was not detected.

These substances were transferred to the rectification column to be purified. Impurities were not detected after the rectification, and the purity of $CH_3F$ was determined to be 99.999 mol % or more.

In the present Examples and Comparative Examples, the mol concentrations of the respective components based on the total amount of the composition were determined as follows by gas chromatographic analysis (GC).

Quantitative analysis was performed using a general internal standard method to determine the concentrations. Difluoro methane (HFC-32) and benzotrifluoride were respectively used as internal standard substances for a low-boiling-point compound and a high-boiling-point compound. Several kinds of standard samples containing known contents (molar ratios) of the internal standard substance and the test sample were analyzed, and a calibration curve of molar ratio versus peak area ratio was plotted. An internal standard substance of a known amount was added to a sample whose fluoromethane content was unknown, and the peak area ratio on the gas chromatogram was measured, thereby calculating the fluoromethane content from the relative mol sensitivity.

Comparative Example

Under the same reaction conditions as those of Example 2, OIME in a gas state was flowed into a reactor filled with a γ-alumina catalyst C containing 1.4 wt % of chlorine, and pyrolyzed. The conversion of OIME was 91%. The composition of the collected reaction product was as follows: 0.001 mol % of methane, 0.0002 mol % of ethylene, 46.49 mol % of $CH_3F$, 0.001 mol % of propylene, 0.004 mol % of methyl chloride, 8.6 mol % of OIME, 44.6 mol % of acid fluoride. The rest was other substances.

The purity after the rectification was 99.9983%, and 0.0013 mol % of methyl chloride and 0.0004 mol % of propylene were contained as impurities.

The invention claimed is:

1. A method for producing fluoromethane, comprising:
   pyrolyzing in a gas phase 1,1,3,3,3-pentafluoro-2-trifluoromethylpropyl methyl ether,
   in the presence of an alumina catalyst to thereby obtain a mixed gas containing fluoromethane and acid fluoride, wherein:
   the alumina catalyst contains chlorine in an amount of 1.0 wt % or less.

2. The method according to claim 1, wherein the catalyst is a γ-alumina catalyst.

* * * * *